US00PP20143P2

(12) United States Plant Patent
Klemm

(10) Patent No.: US PP20,143 P2
(45) Date of Patent: Jun. 30, 2009

(54) ***PETUNIA* PLANT NAMED 'KLEPH07119'**

(50) Latin Name: ***Petunia* hybrid**
Varietal Denomination: KLEPH07119

(75) Inventor: Nils Klemm, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 12/082,160

(22) Filed: Apr. 9, 2008

(51) Int. Cl.
*A01H 5/00* (2006.01)

(52) U.S. Cl. ..... Plt./356

(58) Field of Classification Search ..... Plt./356
See application file for complete search history.

*Primary Examiner*—Susan B. McCormick Ewoldt
(74) *Attorney, Agent, or Firm*—Jondle & Associates, P.C.

(57) ABSTRACT

A new cultivar of *Petunia* particularly characterized by its flowers having a white background with red-purple veins and a dark-purple eye, its compact semi-upright growth habit, and its rain tolerance, is disclosed.

1 Drawing Sheet

Genus and species: *Petunia* hybrid.
Variety denomination: 'KLEPH07119'.

BACKGROUND OF THE NEW PLANT

The present invention comprises a new and distinct cultivar of *Petunia*, botanically known as *Petunia* hybrid, and hereinafter referred to by the cultivar name 'KLEPH07119'. 'KLEPH07119' was discovered as a seedling resulting from a cross conducted in summer 2003 in Stuttgart, Germany between the proprietary female *Petunia* plant, 'V 199' (unpatented) and the proprietary male *Petunia* plant, 'V 019' (unpatented). A single plant selection was subsequently chosen for further evaluation and for asexual propagation.

The new cultivar was created in 2003 in Stuttgart, Germany and has been asexually reproduced repeatedly by vegetative cuttings and in-vitro propagation in Stuttgart, Germany over a four-year period (more than 50 generations). 'KLEPH07119' has been found to retain its distinctive characteristics through successive asexual propagations.

Plant Breeder's Rights for this cultivar were applied for in Canada on Apr. 20, 2007. 'KLEPH07119' has not been made publicly available more than one year prior to filing of this application.

SUMMARY OF THE INVENTION

The following are the most outstanding and distinguishing characteristics of this new cultivar when grown under normal commercial practices in a greenhouse in Stuttgart, Germany.

1. Flowers having a white background, red-purple veins and a dark-purple eye;
2. Compact semi-upright growth habit; and
3. Rain tolerance.

DESCRIPTION OF THE PHOTOGRAPH

This new *Petunia* plant is illustrated by the accompanying photograph which shows the overall plant habit, flowers and foliage; the colors shown are as true as can be reasonably obtained by conventional photographic procedures. The photograph is of a plant about 5-months old and grown from rooted cuttings in a 12-cm pot in a greenhouse (glasshouse) in Stuttgart, Germany under conditions which approximate those generally used in commercial practice.

DESCRIPTION OF THE NEW CULTIVAR

The following detailed descriptions set forth the distinctive characteristics of 'KLEPH07119'. The data which define these characteristics were collected from asexual reproductions carried out in Stuttgart, Germany. The plant history was taken on 5-month-old plants in 12-cm pots that were pinched once approximately one week after potting and grown in a greenhouse in the spring. The color readings were determined under natural light. Color references are to the R.H.S. Colour Chart of The Royal Horticultural Society of London (R.H.S.) (2001).

DESCRIPTION OF THE NEW PLANT

Classification:
- *Family.*—Solanaceae.
- *Genus and species.*—*Petunia* hybrid.
- *Common name.*—*Petunia*.

Parentage:
- *Female parent.*—The proprietary *Petunia* 'V 199' (unpatented).
- *Male parent.*—The proprietary *Petunia* 'V 019' (unpatented).

Plant:
- *Form.*—Compact.
- *Habit.*—Semi-upright.
- *Height* (*from top of soil*).9.0 cm.
- *Width* (*horizontal plant diameter*).—16.0 cm.
- *Propagation.*—Vegetative propagation by terminal tip cuttings or in-vitro propagation of shoot tips.
- *Time to produce a finished flowering plant.*—11 weeks.
- *Time to initiate and develop roots.*—18 days.
- *Root description.*—Moderate density and moderate branching, white roots.

Stems:
- *Average number* (*basal*).—6.
- *Length of basal branches* (*from the base of the stem to the tip*).—9.0 cm.

*Internode length.*—0.5 cm to 2.0 cm.
*Diameter of branches* (*from midpoint*).—5.0 cm to 10.0 cm.
*Stem color.*—RHS 137C.
*Anthocyanin.*—Absent.
*Texture* (*all surfaces*).—Smooth.

Leaves:
*Arrangement.*—Alternate.
*Size.*—Length: 0.5 cm to 2.5 cm. Width: 0.5 cm to 2.0 cm.
*Shape.*—Broadly elliptic.
*Margin.*—Very weak undulation.
*Apex.*—Acute.
*Base.*—Obtuse.
*Immature leaf.*—Color: Upper surface: RHS 138A. Lower surface: RHS 138C.
*Mature leaf.*—Color: Upper surface: RHS 146A. Lower surface: RHS 146B.
*Texture* (*both surfaces*). Smooth.
*Venation.*—Pinnate.
*Venation color.*—Upper surface: RHS 146D. Lower surface: RHS 145A.
*Petioles.*—Length: 0.3 cm to 1.5 cm. Diameter: 0.2 cm. Color (both upper and lower parts): RHS 138B. Texture: Smooth.

Flower bud:
*Shape.*—Irregular to oblong.
*Size.*—Length: 4.0 cm. Diameter: 0.8 cm.
*Color at tight bud.*—RHS 75A and RHS 72A.
*Immature flower color.*—RHS 75A and RHS 72A.
*Texture.*—Pubescent.

Inflorescence:
*Blooming habit* (*flowering season*).—Continuous flowering during the summer.
*Inforescence type.*—Single flower.
*Number of flowers per node.*—1.
*Lastingness of individual blooms on the plant.*—6 days.
*Fragrance.*—Absent.
*Pedicels.*—Color: RHS 137C. Length: 2.0 cm. Diameter: 0.3 cm.
*Texture.*—Smooth.

Flowers:
*Shape.*—Cup-shaped.
*Size.*—Diameter (flower face): 5.5 cm. Depth (total length of flower): 4.0 cm. Funnel: Length: 3.3 cm. Diameter (at opening): 1.0 cm. Outside texture: Smooth.
*Mature flower.*—Face/Margin Color: Upper surface: RHS 71A and RHS 155C. Lower surface: RHS 70B and RHS 155C. Corolla tube: Color inside (throat): RHS 71A. Color outside: RHS 70B. Petals: Apex: Rounded to emarginate. Base: Reniform. Margin: Undulating. Waviness: Low. Lobation: Low. Texture (both surfaces): Smooth.
*Calyx arrangement.*—One star-shaped calyx tube with five sepals fused at the base per flower.
*Sepals.*—Number: 5. Color: Upper surface: RHS 138A. Lower surface: RHS 138B. Length: 2.0 cm. Width: 0.5 cm. Shape: Lanceolate to elliptic. Apex: Obtuse. Base: Fused. Margin: Entire. Texture (both surfaces): Smooth.

Reproductive organs:
*Stamens.*—Quantity: 5. Shape: Needle-like with elliptic head. Filament: Length: 0.5 cm. Diameter: 0.1 cm. Color: RHS 150A. Anther: Shape: Elliptic. Color: RHS 76C. Length: 0.3 cm. Diameter: 0.2 cm. Pollen: Color: RHS 76C. Amount: Abundant.
*Pistils.*—Number: 1. Length: 0.5 cm. Diameter 0.1 cm. Stigma: Color: RHS 150A. Shape: Oval. Length: 1.9 cm. Diameter: 0.1 cm. Style: Color: RHS 150C. Length: 2.0 cm. Diameter: 0.1 cm. Texture: Fibrous.

Fruit and seed set: None observed.
Disease and insect resistance: Not observed.

COMPARISON WITH PARENTAL AND COMMERCIAL CULTIVARS

'KLEPH07119' differs from the female parent, the *Petunia* 'V 199' (unpatented), in that 'KLEPH07119' has a compact semi-upright growth habit, while 'V 199' has a semi-trailing growth habit. In addition, 'KLEPH07119' has a flower with a white background, red-purple veins and a dark-purple eye, while 'V 199' has a pinkish-white flower.

'KLEPH07119' differs from the male parent, the proprietary *Petunia* 'V 019' (unpatented), in that 'KLEPH07119' has a compact semi-upright growth habit, while 'V 019' has an upright growth habit. In addition, 'KLEPH07119' has a flower with a white background, red-purple veins and a dark-purple eye, while 'V 019' has a pure purple flower with white spots. 'KLEPH07119' differs from the commercial comparison variety 'Famous Violet Dark Eye' (unpatented) in that 'KLEPH07119' is more tolerant of rain than 'Famous Violet Dark Eye'.

I claim:

1. A new and distinct cultivar of *Petunia* plant as shown and described herein.

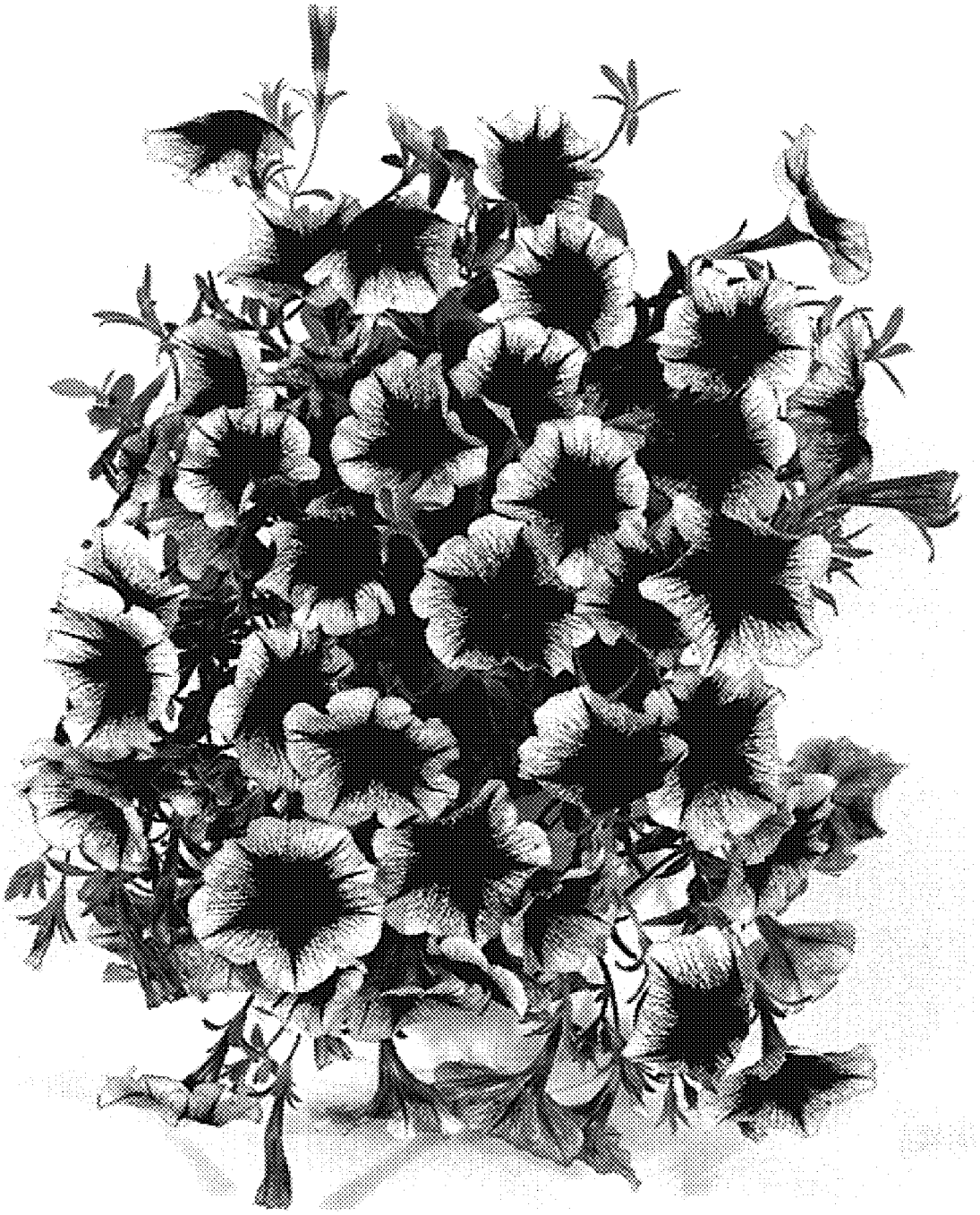

* * * * *